US010254250B2

(12) United States Patent
Udpa et al.

(10) Patent No.: US 10,254,250 B2
(45) Date of Patent: Apr. 9, 2019

(54) ROTATING CURRENT EXCITATION WITH ARRAY MAGNETIC SENSORS NONDESTRUCTIVE TESTING PROBE FOR TUBE INSPECTION

(71) Applicant: BOARD OF TRUSTEES OF MICHIGAN STATE UNIVERSITY, East Lansing, MI (US)

(72) Inventors: Satish S. Udpa, Okemos, MI (US); Lalita Udpa, Okemos, MI (US); Chaofeng Ye, Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 248 days.

(21) Appl. No.: 15/458,703

(22) Filed: Mar. 14, 2017

(65) Prior Publication Data
US 2017/0336360 A1    Nov. 23, 2017

Related U.S. Application Data

(60) Provisional application No. 62/308,040, filed on Mar. 14, 2016.

(51) Int. Cl.
*G01R 1/04*      (2006.01)
*G01N 27/90*    (2006.01)
*G01R 33/09*    (2006.01)

(52) U.S. Cl.
CPC ....... *G01N 27/9033* (2013.01); *G01R 33/093* (2013.01)

(58) Field of Classification Search
CPC ........ G01R 3/00; G01R 1/04; G01R 1/07307; G01R 1/203; G01R 31/2601; G01R 1/067

USPC ............ 324/437, 445–446, 754.01, 324/754.03–754.11, 754.21–755.11, 324/758.01, 690, 696, 724, 149, 220, 221, 324/222, 164, 137; 702/1–199; 73/1.01–36, 488–551

See application file for complete search history.

(56) References Cited

U.S. PATENT DOCUMENTS

2005/0140355 A1*  6/2005  Yamada ............. G01N 27/9033
                                                                     324/137
2005/0206369 A1*  9/2005  Sufka .................... G01P 15/125
                                                                     324/164

(Continued)

OTHER PUBLICATIONS

Diercks et al., "Overview of steam generator tube degradation and integrity issues," Nucl. Eng. Des., 194:19-30 (1999).

(Continued)

*Primary Examiner* — Patrick Assouad
*Assistant Examiner* — Taqi R Nasir
(74) *Attorney, Agent, or Firm* — Marshall, Gerstein & Borun LLP

(57) ABSTRACT

A probe capable of inducing a rotating magnetic field to excite a conductive tube includes an array of magnetic field sensors to detect and characterize defects in the tube. The probe includes a circumferential coil assembly and an axial coil assembly both positioned to induce eddy currents in the conductive tube, such that the magnetic field sensors can detect defects in the tube, including defects extending circumferentially, axially, or any combination thereof, whether at the surface or sub-surface of the tube inner and outer walls.

12 Claims, 14 Drawing Sheets

(56) References Cited

U.S. PATENT DOCUMENTS

| | | | | |
|---|---|---|---|---|
| 2007/0200562 | A1* | 8/2007 | Shimomura | G01V 3/102 |
| | | | | 324/222 |
| 2009/0206830 | A1* | 8/2009 | Kim | G01N 27/9033 |
| | | | | 324/220 |
| 2011/0062946 | A1* | 3/2011 | Peng | G01N 27/902 |
| | | | | 324/149 |
| 2013/0009632 | A1* | 1/2013 | Yamamoto | G01N 27/9046 |
| | | | | 324/222 |
| 2013/0214768 | A1* | 8/2013 | Chintamaneni | G01N 27/72 |
| | | | | 324/222 |
| 2013/0214769 | A1* | 8/2013 | King | G01N 27/22 |
| | | | | 324/222 |

OTHER PUBLICATIONS

Diercks et al., "Steam generator tube integrity program," Nucl. Eng. Des., 165:143-149 (1996).

Fukutomi et al., "Remote field eddy current technique applied to non-magnetic steam generator tubes," NDT E Int., 34:17-23 (2001).

Hamia et al., "Eddy-Current Nondestructive Testing Using an Improved GMR Magnetometer and a Single Wire as Inducer: A FEM Performance Analysis," IEEE Trans. Magn., 46(10):3731-3737 (2010).

Joubert et al., "Multi-detector eddy current probe for the non-destructive evaluation of steam generator tubes, designed for an imaging approach," in Electromagnetic Nondestructive Evaluation (iii), 15:34-44 (1999).

Lee et al., "Prediction of crack growth in steam generator tubes using Monte Carlo simulation," CMES 11(1):9-16 (2006).

Liang et al., "Investigation of overheating of the final super-heater in a 660 MW power plant," Eng. Fail. Anal., 45:59-64 (2014).

Obrutsky et al., "Transmit receive eddy current probes," pp. 167-175 (1996).

Pham et al., "A model for the forward problem in magnetic induction tomography using boundary integral equations," IEEE Trans. Magn., 44(10):2262-2267 (2008).

Postolache et al., "GMR array uniform eddy current probe for defect detection in conductive specimens," Measurement, 46:4369-4378 (2013).

Raj et al., "NDE methodologies for characterisation of defects, stresses and microstructures in pressure vessels and pipes," Int. J. Press. Vessels Pip., 73:133-146 (1997).

Sedighi et al., "A novel application of a neuro-fuzzy computational technique in modeling of thermal cracking of heavy feedstock to light olefin," Rsc Adv., 4:28390-28399 (2014).

Smith et al., "GMR magnetic sensor arrays for NDE eddy-current testing," in AIP Conference Proceedings, 657:419-426 (2003).

Takagi et al., "Electromagnetic NDE research activities in JSAEM," in Electromagnetic Nondestructive Evaluation, 12:9-16 (1997).

Valentino et al., "GMR Second Order Electronic Gradiometer as Eddy Current Probe in NDE Applications," Review of Quantiative Nondestructive Evaluation 28: 350-354 (2009).

Xin et al., "Nondestructive Inspection Using Rotating Magnetic Field Eddy-Current Probe," IEEE Trans. Magn., 47(5):1070-1073 (2011).

Xin et al., "Rotating field eddy current probe with bobbin pickup coil for steam generator tubes inspection," Ndt E Int., 54:45-55 (2013).

Xin, "Design and analysis of rotating field eddy current probe for tube inspection," A Dissertation, Michigan State University (2014).

Xu et al., "Total and reduced magnetic vector potentials and electrical scalar potential for eddy current calculation," Ieee Trans. Magn., 40(2):938-940 (2004).

Yang et al., "Rotating Field EC-GMR Sensor for Crack Detection at Fastener Site in Layered Structures," IEEE Sens. J., 15(1):463-470 (2015).

Ye et al., "Differential Sensor Measurement with Rotating Current Excitation for Evaluating Multilayer Structures," IEEE Sens. J., 16(3):782-789 (2016).

Ye et al., "Magnetoresistive Sensor with Magnetic Balance Measurement for Inspection of Defects under Magnetically Permeable Fasteners," IEEE Sens. J., 16(8):2331-2338 (2016).

Ye et al., "Novel Rotating Current Probe with GMR Array Sensors for Steam Generate Tube Inspection," 9 pages (2016).

Ye et al., "Novel Transceiver Rotating Field Nondestructive Inspection Probe," IEEE Trans. Magn., 51(7):1-6 (2015).

Ye et al., "Three Phase Rotating Field Eddy Current Probe," Electromagn. Nondestruct. Eval. XVIII, 40:337-345 (2015).

Zeng et al., "Finite-Element Model for Simulation of Ferrite-Core Eddy-Current Probe," IEEE Trans. Magn., 46(3):905-909 (2010).

Zeng et al., "Reduced Magnetic Vector Potential Formulation in the Finite Element Analysis of Eddy Current Nondestructive Testing," IEEE Trans. Magn., 45(3): 964-967 (2009).

\* cited by examiner

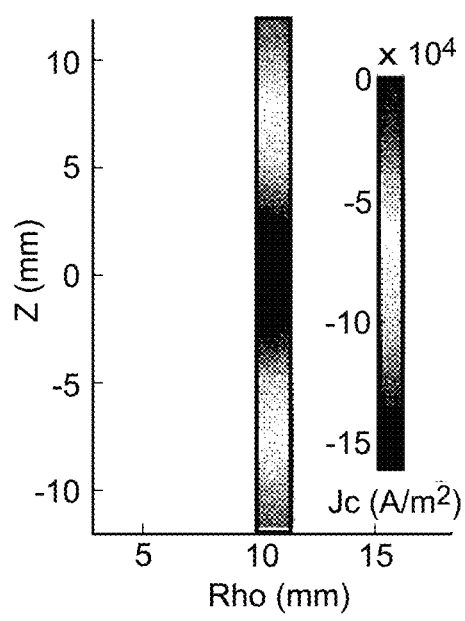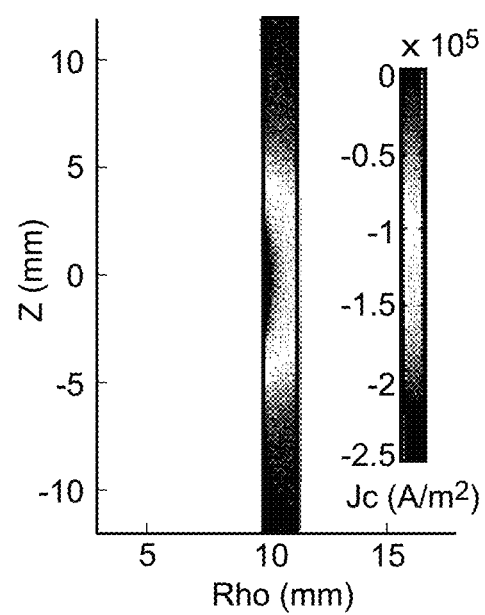
FIG. 2A                    FIG. 2B

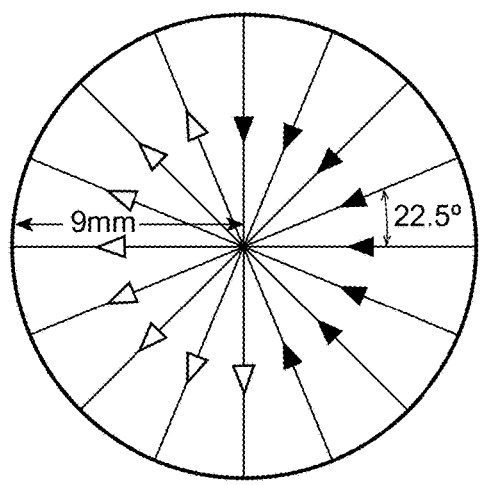
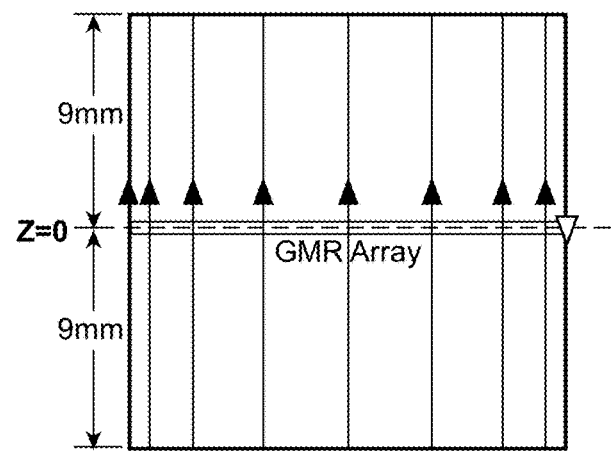
FIG. 3A                      FIG. 3B

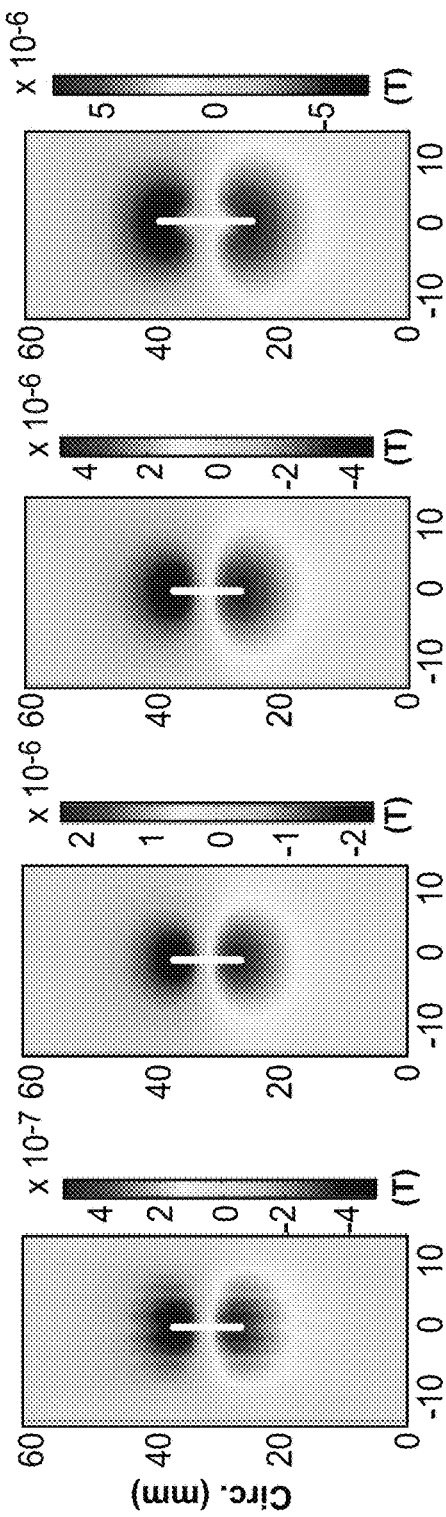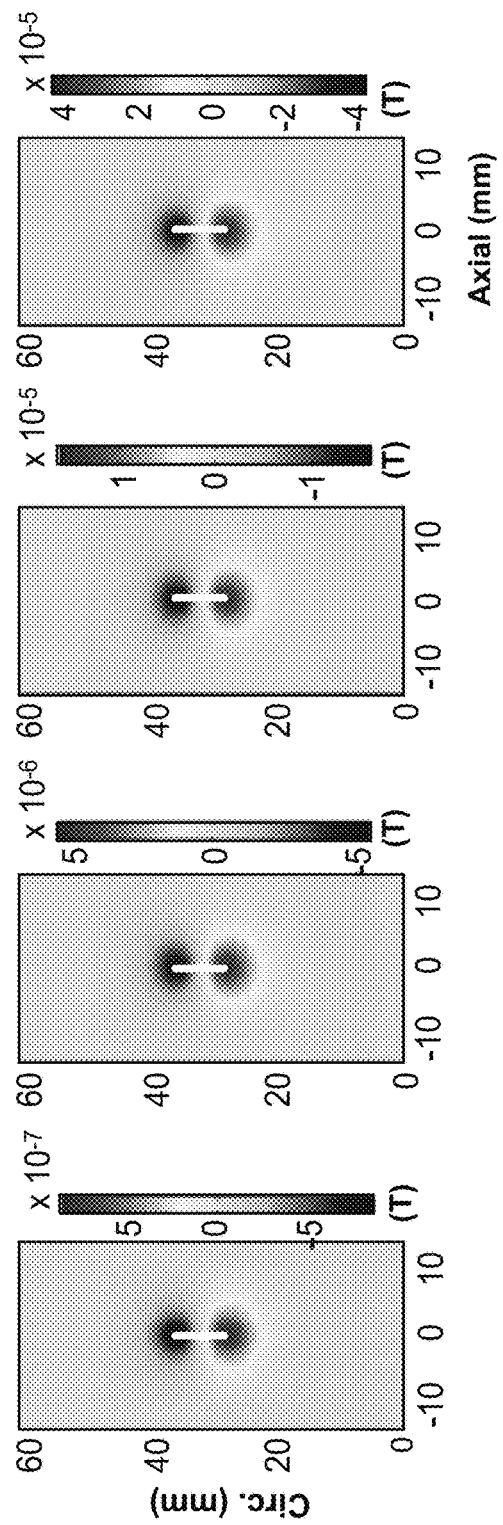
FIG. 9

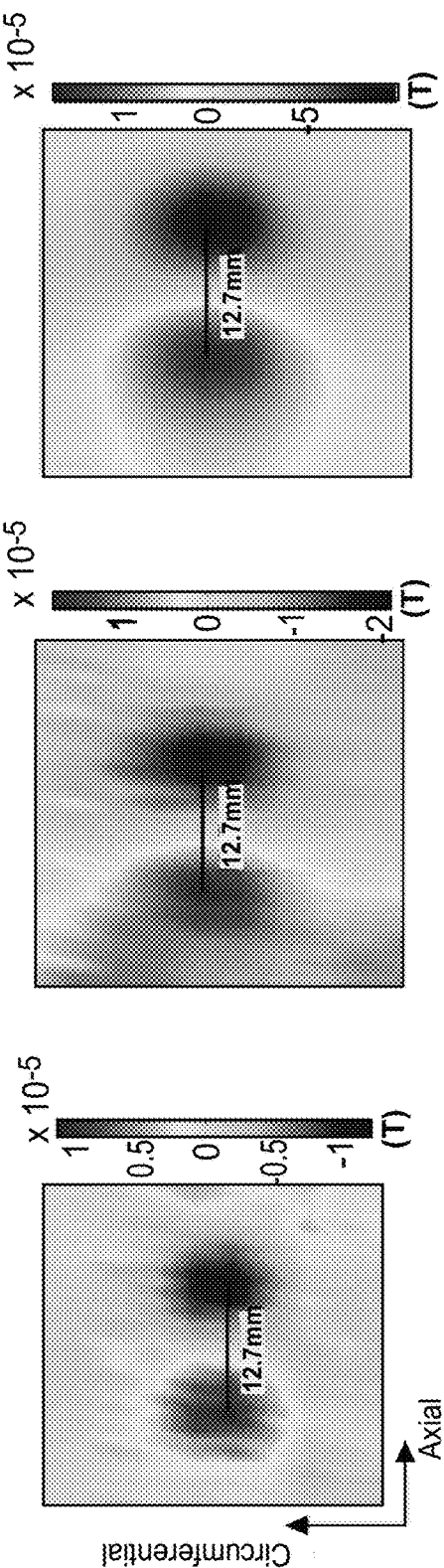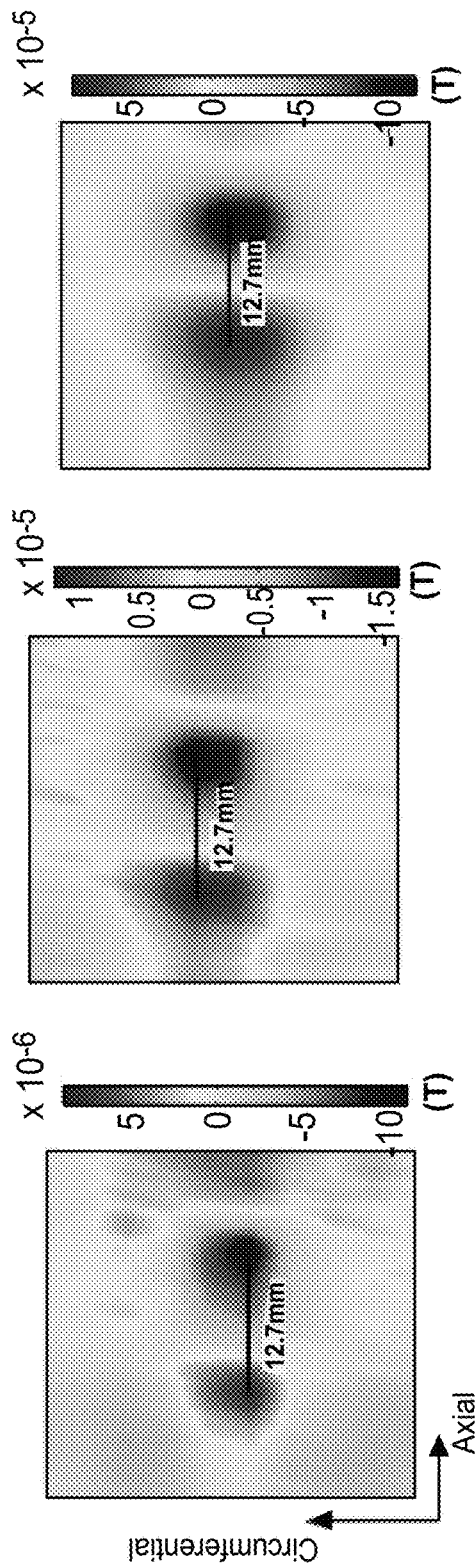
FIG. 13A  FIG. 13B  FIG. 13C
FIG. 13D  FIG. 13E  FIG. 13F

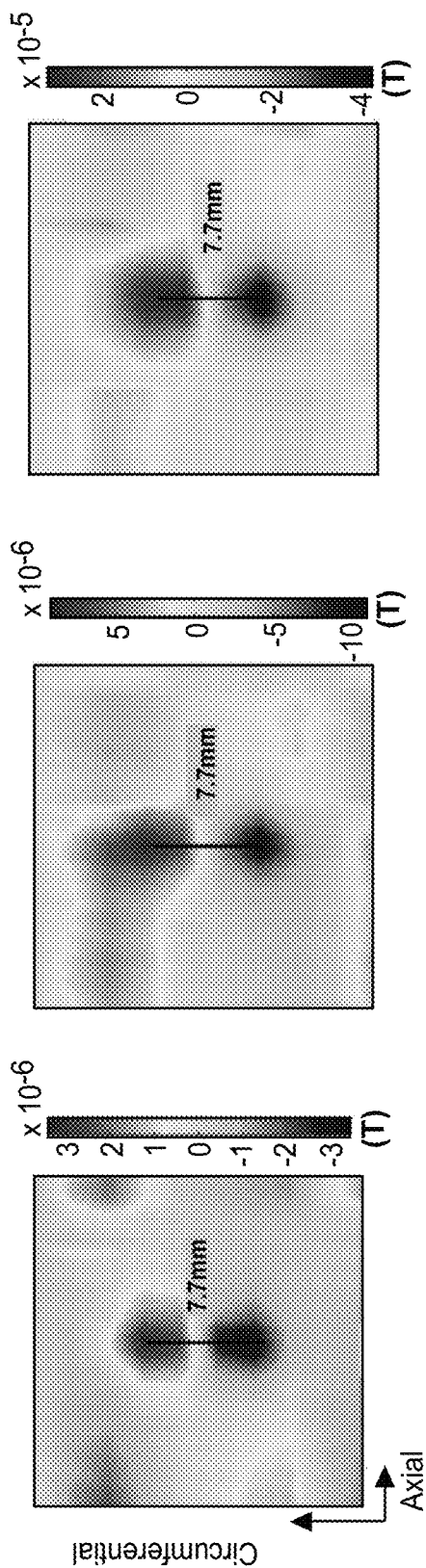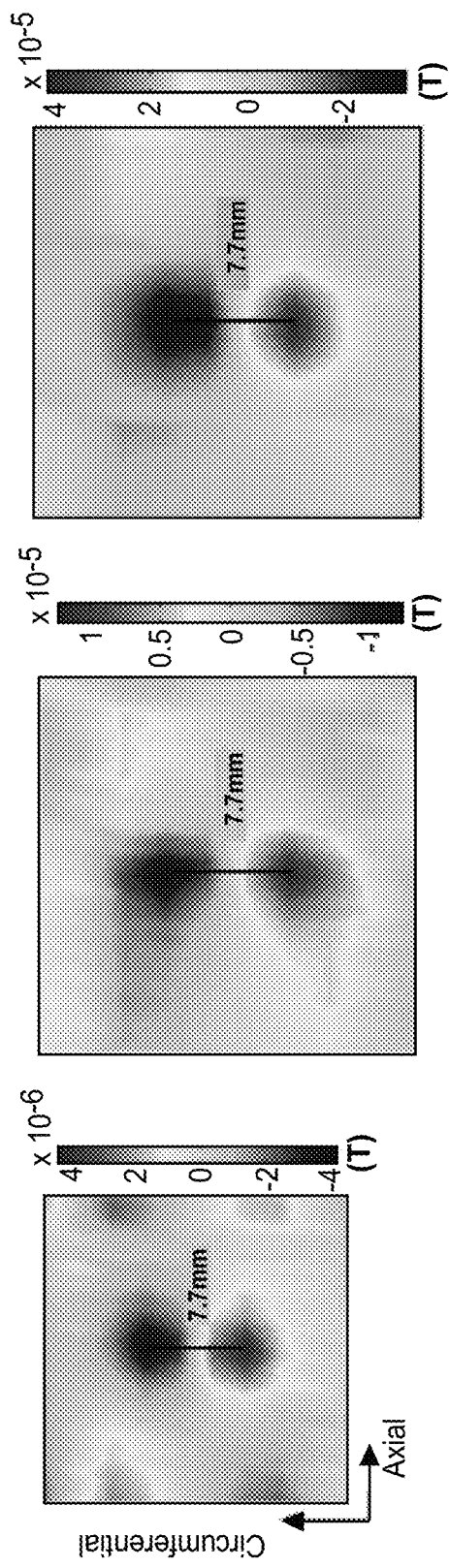

ROTATING CURRENT EXCITATION WITH ARRAY MAGNETIC SENSORS NONDESTRUCTIVE TESTING PROBE FOR TUBE INSPECTION

CROSS-REFERENCE TO RELATED APPLICATION

This application is claims the benefit of U.S. Application Ser. No. 62/308,040, filed Mar. 14, 2016, entitled "Rotating Current Excitation with Array Magnetic Sensors Nondestructive Testing Probe For Tube Inspection," which is hereby incorporated by reference in its entirety.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Industrial units, particularly those in the chemical, nuclear, power and petrochemical industries, employ hundreds of miles of tubing/piping. In all these applications the tubing/piping is often exposed to corrosive environments and, consequently, industries are interested in assessing the integrity of these tubes periodically. Tubing, for example, is critically important in nuclear power plants, where steam generator tubes are used to transfer thermal energy and to isolate a radioactive region from the rest of the facility. Each nuclear power plant can have 2-4 steam generators with over 3000 tubes in each generator. These tubes are continuously exposed to high temperature and pressure resulting in various types of degradation including mechanical wear, stress corrosion cracking, pitting, wall thinning, denting and inter granular attack. Concern for the operational safety of the power plants, requires periodic inspection of steam generator tubes.

Steam generator tube inspection techniques using eddy current probes have evolved over the years in an attempt to improve the speed and reliability of inspection. Eddy current inspection probes, such as bobbin coil probes, rotating probe (Rotating Pancake Coils and Plus-Point), and array probes (X-Probe, Smart Array Probe and Intelligent Probe), have been used widely for detecting and characterizing flaws in the tube wall. Bobbin coil probes offer high operational speed, but are unable to detect circumferential cracks. Rotating probes can provide a C-Scan image of tube wall and can offer a superior ability to characterize and size both axial and circumferential defects. However, the helical scanning process is slow and prone to probe wear, and the mechanical control system for probe rotation is complex and susceptible to failure. Array probes provide high inspection speed, but they need sophisticated excitation and post-processing schemes.

There is a need for a fast, robust, highly-efficient tube inspection probe.

SUMMARY OF INVENTION

The present application describes probe designs that use a rotating current excitation scheme and magnetic sensors for inspecting conduits, such as tubing and piping. Rotating eddy currents in a tube wall are induced using a pair of axial and circumferential excitation coils used to form the probe. A circumferential array of sensors, e.g., giant magnetoresistance (GMR) sensors, is provided and used to measure a radial component of the magnetic field. A perturbation in eddy current flow caused by a defect produces a radial component field that is measured by these GMR sensors. The probe moved along an axial direction induces a magnetic field in the tube wall that is used to detect defect location and orientation. The probe is thus sensitive to both axial and circumferential defects and offers the advantages of high sensitivity over a wide frequency range.

In accordance with an example, an eddy current detection probe comprises: a circumferential coil assembly formed of a plurality of circumferentially extended coil windings, each circumferentially extended coil winding being spaced from adjacent circumferentially extended coil windings by a spacing distance, the circumferential coil assembly being positioned on an outer portion of the probe to induce circumferentially-extending eddy currents in a conductive vessel upon generating a circumferentially-probing magnetic field; an axial coil assembly formed of a plurality of axially extended coil windings, each axially extended coil winding being radially spaced apart from adjacent axially extended coil windings, the axial coil assembly being positioned on an outer portion of the probe to induce axially-extending eddy currents in the conductive vessel upon generating an axially-probing magnetic field, the circumferential coil assembly and the axial coil assembly being configured to receive respective current drive signals for generating the magnetic field; and a magnetic sensor array for detecting circumferentially-extending eddy currents and axially-extending eddy currents.

BRIEF DESCRIPTION OF THE DRAWINGS

The figures described below depict various aspects of the system and methods disclosed herein. It should be understood that each figure depicts an example of aspects of the present systems and methods.

FIGS. 2A and 2B illustrate the in-phase (A) and quadrature (B) components of a circumferential eddy current density induced by a circumferential coil, in accordance with an example simulation of a probe.

FIG. 3A illustrates a top view of an example axial coil assembly, in accordance with an example probe. FIG. 3B illustrates a side view of the axial coil assembly of FIG. 3A.

FIG. 9 illustrates simulation results obtained with circumferential notches of different depths: ⅛, ⅜, ⅝, and ⅞ of the tubular wall. The top row shows the real component, the bottom row shows the imaginary component.

FIGS. 13A-13F illustrate C-scan data of axial notches using the probe of FIG. 11 showing the real component of 60% (FIG. 13A), 80% (FIG. 13B), and 100% (FIG. 13C) and quadrature component of 60% (FIG. 13D), 80% (FIG. 13E), and 100% (FIG. 13F).

FIGS. 14A-14F illustrate C-scan data of circumferential notches using the probe of FIG. 11 showing the real component of 60% (FIG. 13A), 80% (FIG. 13B), and 100% (FIG. 13C) and quadrature component of 60% (FIG. 13D), 80% (FIG. 13E), and 100% (FIG. 13F).

DETAILED DESCRIPTION

Figure 1:
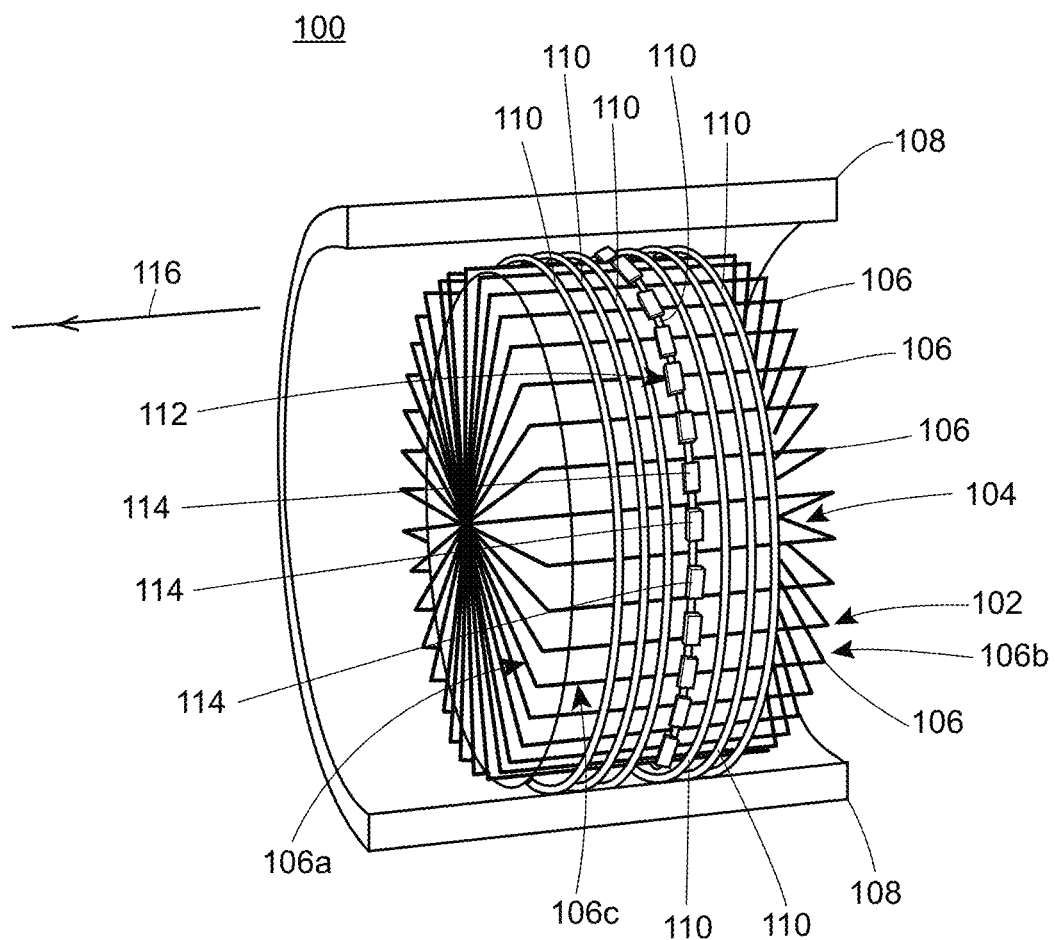
FIG. 1 illustrates an inspection probe with circumferential and axial excitation coil assemblies and magnetic field sensors for tube inspection, in accordance with an example.

The present application describes a variety of eddy current probes developed for inspecting structural components as part of routine maintenance procedures, as well as for controlling quality. A particular issue of interest to industry is the inspection of tubular goods. Bobbin coil probes, which offer fast scanning speed (~1 m/sec), are mainly used for initially detecting regions of possible degradation. These regions are subsequently inspected using other types of probes to gain additional information or clarity. Bobbin coil probes are not suitable for detecting circumferential defects in tubes, since the induced eddy currents are parallel to the crack orientation, rendering them insensitive to such defects. Rotating probes can provide an image (e.g., a two-dimensional image such as a C-Scan) of the tube wall with high resolution. However, the high lift-off sensitivity of such probes could result in spurious responses that could obscure the true defect signal. Additionally, the helical scanning process is time-consuming, prone to additional probe wear, and the mechanical control system for rotation is complex and susceptible to failure. Array probes offer high inspection speed and resolution, but they need sophisticated excitation and post-processing schemes. Further, their signal is commonly contaminated by noise introduced as a consequence of probe vibration during the inspection process. Rotating magnetic field probes have been studied for tube inspection. These probes generate a rotating field without mechanically rotating the coils. This probe shares the advantage of high inspection speed with bobbin probes and is additionally sensitive to cracks of all orientations. However, rotating field probes only generate one dimensional (1D) scan data, not a C-scan image for visualization of defects. Such probes will not distinguish between single and multiple defects at the same axial location.

The present disclosure addresses these deficiencies and provides novel probe designs that use rotating current excitation and magnetic field array sensors for nonferromagnetic tube inspection. The probe designs induce rotating eddy currents in the tube wall under examination, using axially- and circumferentially-oriented coils. An array of magnetic field sensors may be located circumferentially to measure the induced magnetic field. The perturbation in eddy current flow produces a field that is measured by the magnetic field sensors in the presence of a defect. A C-scan image can be obtained with a line scan. Information from the C-scan can be employed to determine the location of the defect, its orientation, as well as its size. The probes are sensitive to defects in all orientations. The probes are able to scan much faster than an array probe since they do not employ a transmit-receive configuration. The probes are also faster than mechanically rotating probes, since there is no circumferential movement of the probe.

The excitation and data acquisition systems associated with the probe can be implemented in a less complex manner compared to those required for array probes. Moreover, the probes offer fine spatial resolution and high sensitivity over a wide range of frequencies.

FIG. 1 illustrates a probe 100 having two coil assemblies, an axial coil assembly 102 and a circumferential coil assembly 104. The axial coil assembly 102 is formed of a plurality of coil windings 106, each having an upper radial segment 106a, a lower radial segment 106b, and two axial extending segment 106c. The radial segments 106a and 106b and the two axial segments 106c form a continuous electromagnetic coil winding that extends laterally across the probe 100 and that extends along an axial length of the program 100. The amount of axial extent is defined by the length the segments 106c, and the length determines the amount of axial distance the probe can scan of a tube wall 108, at any given scan position. As the probe 100 is moved axially within the tube wall 108, the probe 100 can scan along other axial positions and thus can scan over a greater axial distance. But at any given static position of the probe, the axial scanning range is defined by the length of the segments 106c.

In addition to the axial coil assembly 102, the probe 100 includes the circumferential coil assembly 104 formed a plurality of circumferential coil windings 110, each an electromagnetic conductive loop centered around an axial center 112 of the probe 100 and each spaced apart from each adjacent coil 110 by an axial spatial distance. In the illustrated example, the probe 100 includes seven (7) circumferential coil windings 110, although any number of coil windings may be used for the assembly 104, which is also the case for the axial assembly 102. The windings 110 of the assembly 104 may be positioned interior to the windings 106 of the assembly 102, or the windings 110 may be on the exterior, encircling the assembly 102. In the illustrated example, the windings 110 are equally spaced from each other. In other examples, the coil spacing may vary, periodically or aperiodically. For example, the coil spacing may be a particular spacing distance between some coils and a harmonic of that spacing distance between other coils. The same is true for the coil windings 106.

In the illustrated example, a sensor stage 112 is provided for the probe 100, where the sensor stage 112 is formed of a plurality of magnetic sensors 114 provided around a circumferential periphery of the probe 100. The sensors 114 are an array of giant magnetoresistance (GMR) sensors, in the illustrated example. Sensors 114 may be positioned adjacent to or connected to one of the circumferential windings 110, as shown.

In operation, a controller provides electrical signals to the windings 106 and 110, which then produce magnetic fields corresponding to an axial extent of the tube wall and circumferential extent of the tube wall 108. In response, rotating eddy currents can be induced in the tube wall 108, in particular, at points of a defect, such as a fissure, notch, opening, thickened region, etc. By way of example, the defects may be surface defects on an inner surface of the wall 108. The defects may be entirely subsurface, i.e., in the interior of the tube wall 108. The defects may extend from a surface to an interior of the tube wall 108. The sensor stage 112 measures the radial position of the magnetic field within the tube wall 108. As the probe 100 is moved axially within the tube wall 108, the sensor stage 112 can measure the radial extent of the defect, as well as the axial extent of the defect. For example, a defect that extends in the tube wall 108 like a coil, having a length that snakes radially and axially, will be detected continuously along its entire length, using the probe 100.

Two excitation coil assemblies 102 and 104, oriented along axial and circumferential directions, respectively, are designed so that the respective coil windings are perpendicular to each other at every intersection. The currents in the two coils can be written as:

$$I_c = I_{0c} \cos(\omega t) \quad (1)$$

$$I_a = I_{0a} \cos(\omega t + 90°) \quad (2)$$

where $I_c$ is the current in the circumferential coil assembly 104, $I_a$ the current in the axial coil assembly 102, $\omega$ the angular frequency, $I_{0c}$ and $I_{0a}$ are amplitudes of the circumferential and axial current respectively. The magnetic field generated by the coils 102 and 104 is sinusoidal in time, and so are the induced eddy currents in the sample tube wall 108.

The total eddy current ($J_{eddy}$) in the tube wall 108 can be written as $$J_{eddy} = \bar{J}_c \hat{\varphi} + \bar{J}_z \hat{z} \quad (3)$$

where z are unit vectors in the cylindrical coordinate system, $\bar{J}_c$ and $\bar{J}_z$ are the circumferential and axial eddy current density phasors, which are about 90° apart in phase.

The currents induced by the axial and circumferential excitation interact to produce locally circulatory or rotational currents. The rotational nature of the currents ensures that they are perturbed by defects irrespective of whether they are axial or circumferentially oriented.

The circumferential sensor (GMR sensors) array 112 is positioned in the probe 100 to measure the radial component of induced magnetic field ($\bar{B}_r$). In the presence of a defect, the perturbation in eddy current flow produces extra radial component magnetic field that is measured by the GMR sensors 114. As the probe 110 scans along axial direction inside tube a C-scan image is generated.

GMR sensors 114 offers high sensitivity over a wide range of frequencies from DC to the megahertz range (e.g., to 1 MHz, to 10 MHz, to 100 MHz, or to 1000 MHz). The probe design 110 is able to achieve very high spatial resolution. Even greater resolution (micro-meter) can be achieved depending on the fabrication techniques and probe coil assembly dimensions, for example, from using microfabrication technologies to integrate sensors onto a signal chip.

To examine operation of probe designs according to some examples, a three-dimensional (3D) finite element model was developed to simulate the underlying physical process and predict the response of the probe for different defects.

The formulation applied a reduced magnetic vector potential formulation. A magnetic vector potential A is split into $A_s$ and $A_r$, where $A_s$ is the magnetic vector potentials due to the source in free space and $A_r$ is the reduced magnetic vector potential due to the induced current in the conducting material. The governing equation for eddy current induction is given by Equation (4).

$$-\nu \nabla^2 A_r + j\omega \sigma A_r = (1-\nu_r)\nabla \times H_s - j\omega \sigma A_s \quad (4)$$

In the equation, $\nu$ is the reluctivity, $\nu_r$ the relative reluctivity, $\sigma$ the conductivity, $\omega$ the angular frequency, and $H_s$ the magnetic density due to the source in free space. The source variables on the right hand side $A_s$ and $H_s$ can be computed analytically. The formulation eliminates the need for generating a mesh for the excitation coils as they step through during the scanning process. The tube and excitation coils of the rotating field probe are modeled and meshed separately. The tube geometry was modeled corresponding to a free span region in a steam generator, with an inner and outer radius of the simulated tube is 9.85 mm, and 11.45 mm, respectively. The tube material is Inconel 600, with conductivity of $9.69*10^5$ S/m.

Induced eddy currents in a defect free tube wall were calculated using the simulation model. According to the superposition principle, the circumferential and axial exciting currents were considered independently. First, the induced eddy current due to the circumferential coil was calculated. The circumferential coil consists of uniformly distributed wires. The current in the circumferential coil was given by $I_c = \cos(2\pi f t)$, where f=30 kHz. The excitation frequency, 30 kHz, is chosen so as to ensure adequate skin depth to penetrate the tube wall thickness. The eddy currents induced by the circumferential coil flows circumferentially in the tube wall. The in-phase (real) and quadrature (imaginary) component of the circumferential eddy current density in the tube wall according to an example of the model is presented in FIGS. 2A and 2B.

The axial coil was also simulated using the model. The top and lateral views of the axial coil are as shown in FIGS. 3A and 3B. The current in the axial coil is $I_a = \cos(2\pi f t + 90°)$, where f=30 kHz. The induced current in the tube wall due to the axial coil flows in the axial direction near z=0 plane where the GMR sensors are located. The in-phase and quadrature component of axial direction eddy current density measured on the z=0 plane are shown in FIGS. 4A and 4B.

Figure 4A:
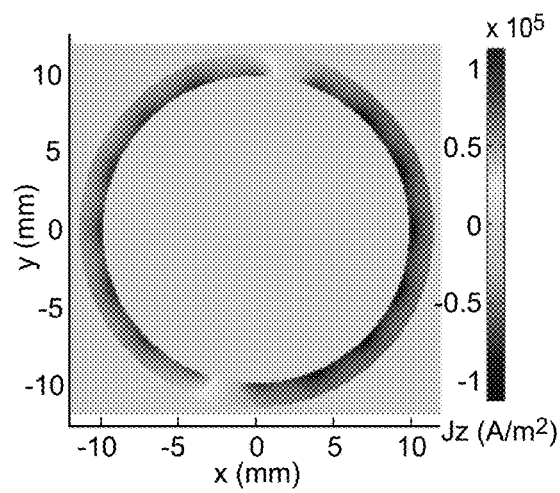
FIGS. 4A and 4B illustrate the in-phase (A) and quadrature (B) components of an axial eddy current density induced by an axial coil assembly, in accordance with an example simulation of a probe.
Figure 4B:
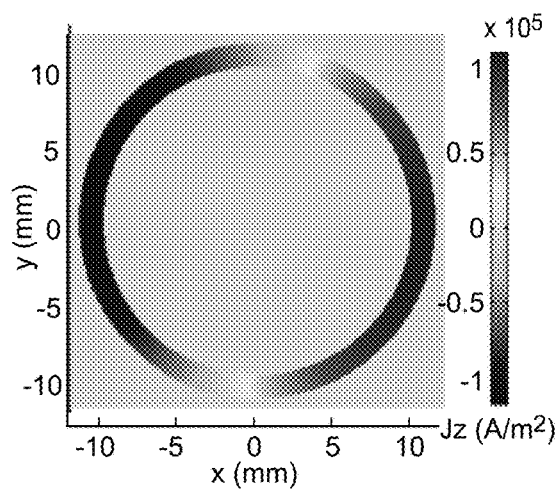
Figure 5A:
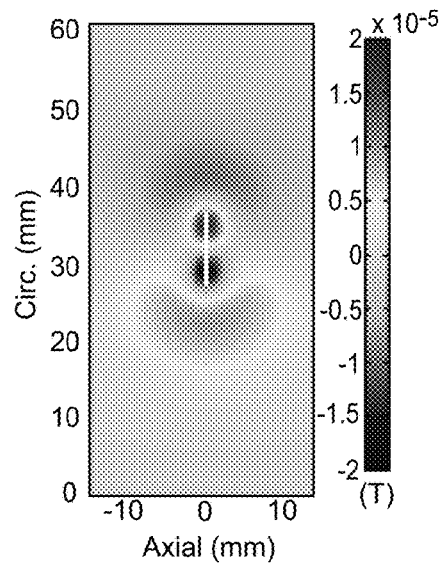
FIGS. 5A and 5B illustrate simulation results obtained from a circumferential notch defect in a tubular wall, showing the real and imaginary components, respectively.
Figure 5B:
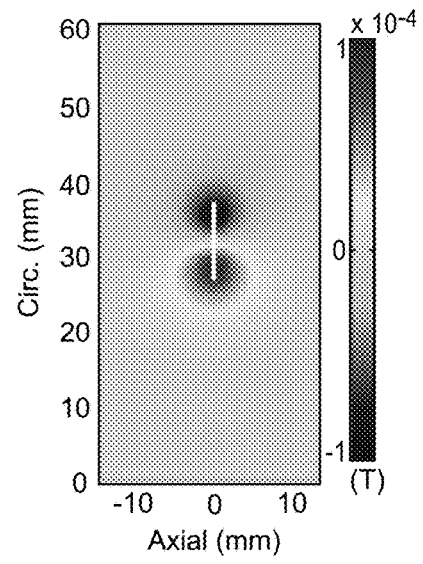
Figure 6A:
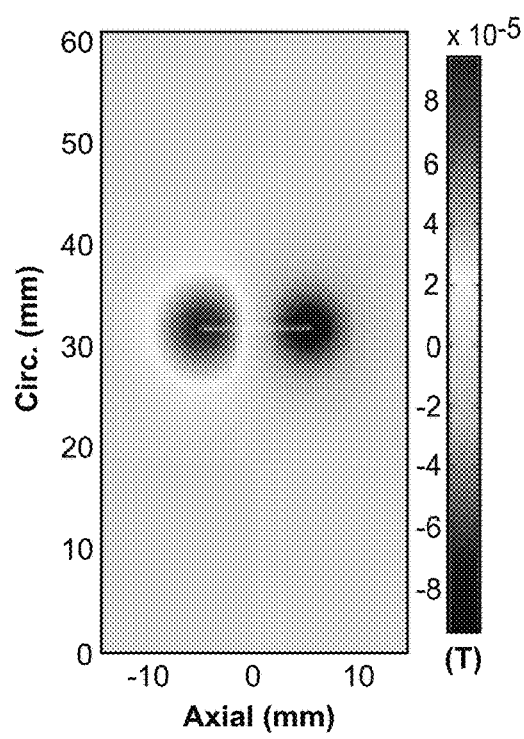
FIGS. 6A and 6B illustrate simulation results obtained from an axial notch defect in a tubular wall, showing the real and imaginary components, respectively.
Figure 6B:
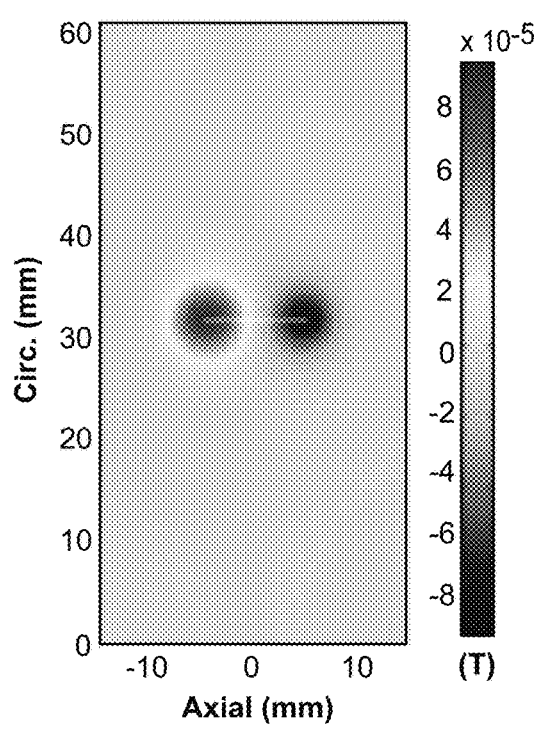

From the results presented in FIGS. 4A and 4B, it is seen that the axial induced current is largely uniform except in the area where the excitation current changes direction. The dead zone created as a consequence made the probe insensitive to circumferentially oriented defects in the small region. Note the length along the circumference where the eddy current density drops to less than 36.8% (1/e) of average value is about 4.8% of the circumference. Defects longer than 4.8% of the circumference that lie in the dead zone can be detected. A simple way to obtain full circumferential coverage, two axial coils that are shifted relative to each other can be used. To full coverage of small circumferential defect, two axial coils that are shifted relative to each other can be used.

A 3D finite element (FEM) model was used to predict the radial component of induced magnetic flux density measured by the GMR-based probe due to defects of different size, orientation, and location in the tube wall.

Axial and circumferential notch defects were analyzed using the model. An axial notch of length 12 mm and width 0.4 mm, and a circumferential notch of length 7.7 mm and width 0.5 mm were machined in the tube wall. The depths of both notches were 100% of the tube wall. The notches were located at z=0 mm. The circumferential and axial coils were excited by a sinusoidal current source at 30 kHz frequency.

The simulation results showing the real and imaginary parts of the fields due to axial and circumferential notches are presented in FIGS. 5A and 5B and FIGS. 6A and 6B, respectively. As shown, both circumferential and axial notches are detected by the probe design. Furthermore, the magnitude of the signals from axial and circumferential notches are comparable which implies that the probe has similar sensitivity to defects with different orientations. For both notches, there are two lobes in the C-scan image due to currrents bending around the defect. The orientation of the defect is also evident from the location of the positive and negative peaks of the C-scan data in FIGS. 5A and 5B and FIGS. 6A and 6B.

Figure 7A:
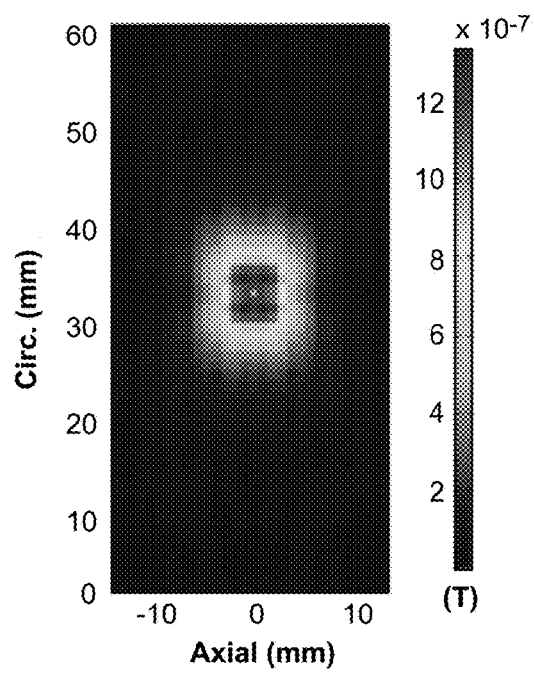
FIGS. 7A-7C illustrate simulation results obtained for different length circumferential notch defects in a tubular wall, FIG. 7A for a 1 mm defect, FIG. 7B for a 2.5 mm defect, and FIG. 7C for a 5 mm defect, each defect being 1 mm in width.
Figure 7B:
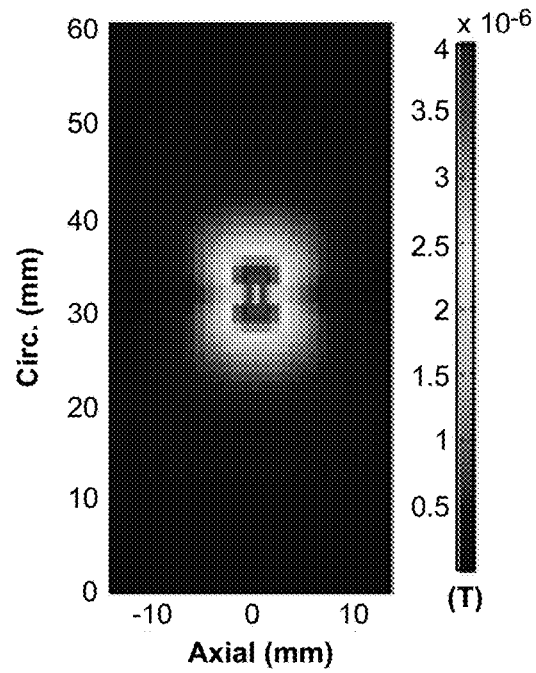
Figure 7C:
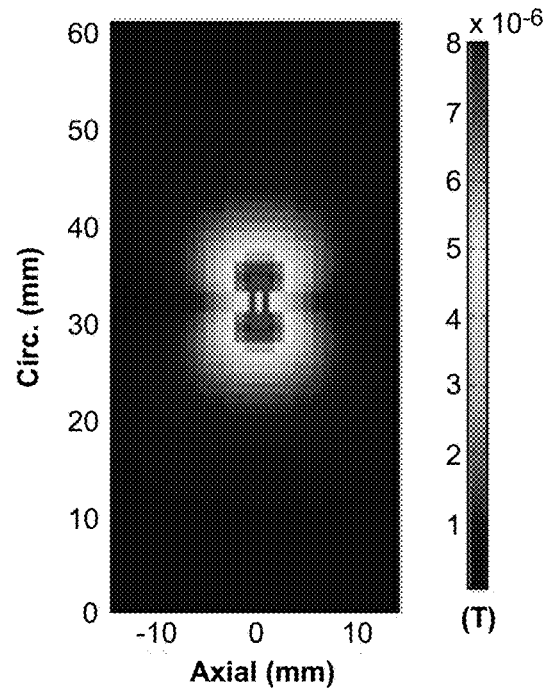
Figure 8:
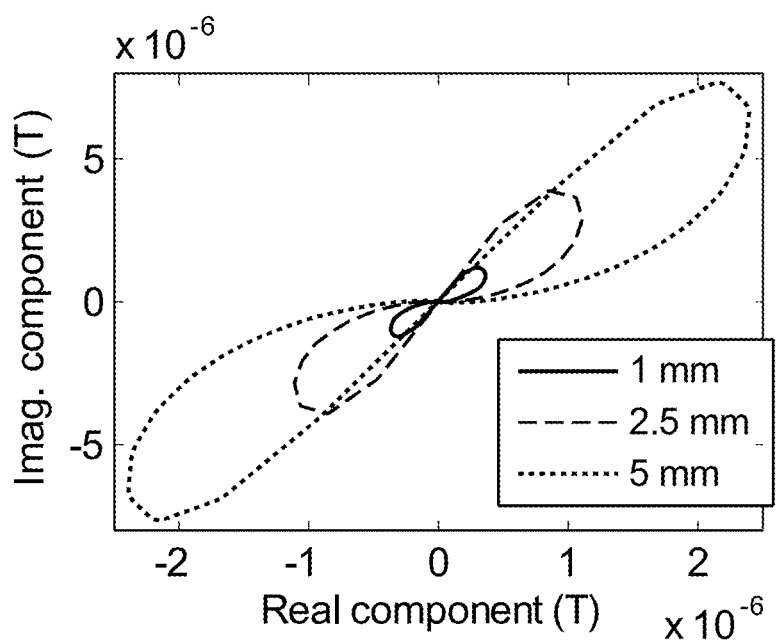
FIG. 8 illustrates simulation results obtained with a 50% tubular wall outer diameter circumferential notch with a width of 1 mm and at different lengths. A Lissajous pattern is shown derived from the real and imaginary components measured along the circumferential direction.

The effect of defect length was also examined using the probe model. Circumferential notches located on the outside diameter (OD) of tube wall with lengths varying from 1 mm to 5 mm were simulated. The depth of the notch was 50% of the tube wall (TW) and having a width is 1 mm. The simulation results are shown in FIGS. 7A-7C. FIG. 8 is the corresponding Lissajous Patterns of real and imaginary component of the data on the line scan at Z=0 mm. As shown, the magnitude of the signal is positively correlated with the defect length.

Figure 10:
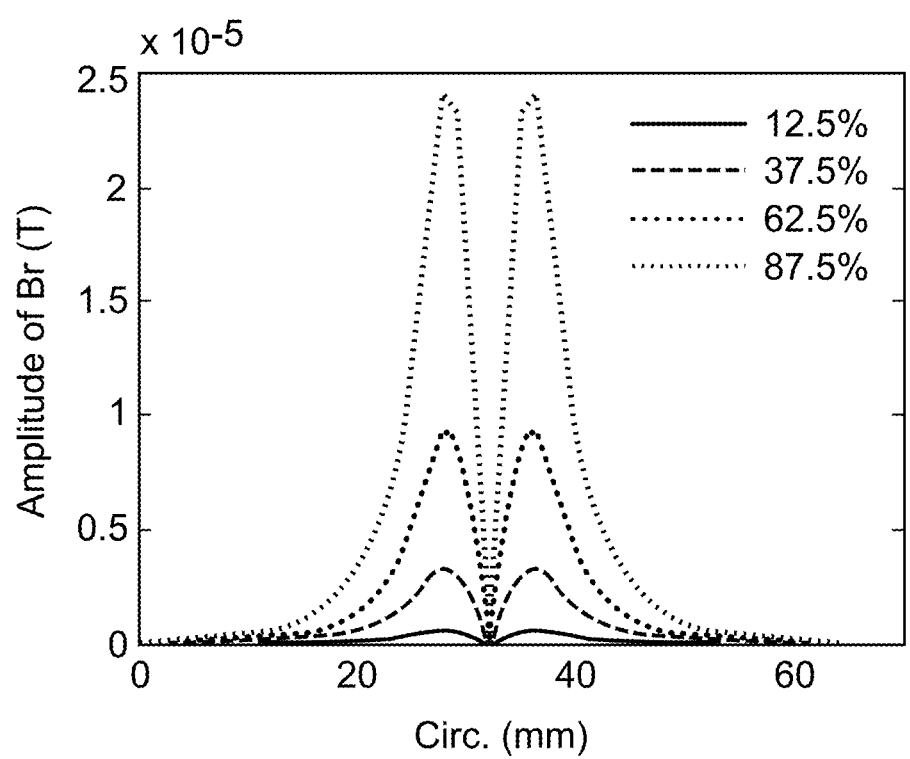
FIG. 10 illustrates simulation results obtained with circumferential notches of different depths, showing the amplitude and circumferential direction.

Notch depths were also examined. OD circumferential notches (length 7.7 mm×width 0.4 mm) with different depths (varying from 12.5% to 87.5% of the tube wall) were simulated. The corresponding simulation results are shown in FIG. 9. Further FIG. 10 shows the amplitude of the radial component of induced magnetic field ($\overline{B}_r$) along the circumferential scan at axial location, Z=0 mm. It can be seen that the magnitude of the signal is positively correlated with defect depth.

Figure 11:
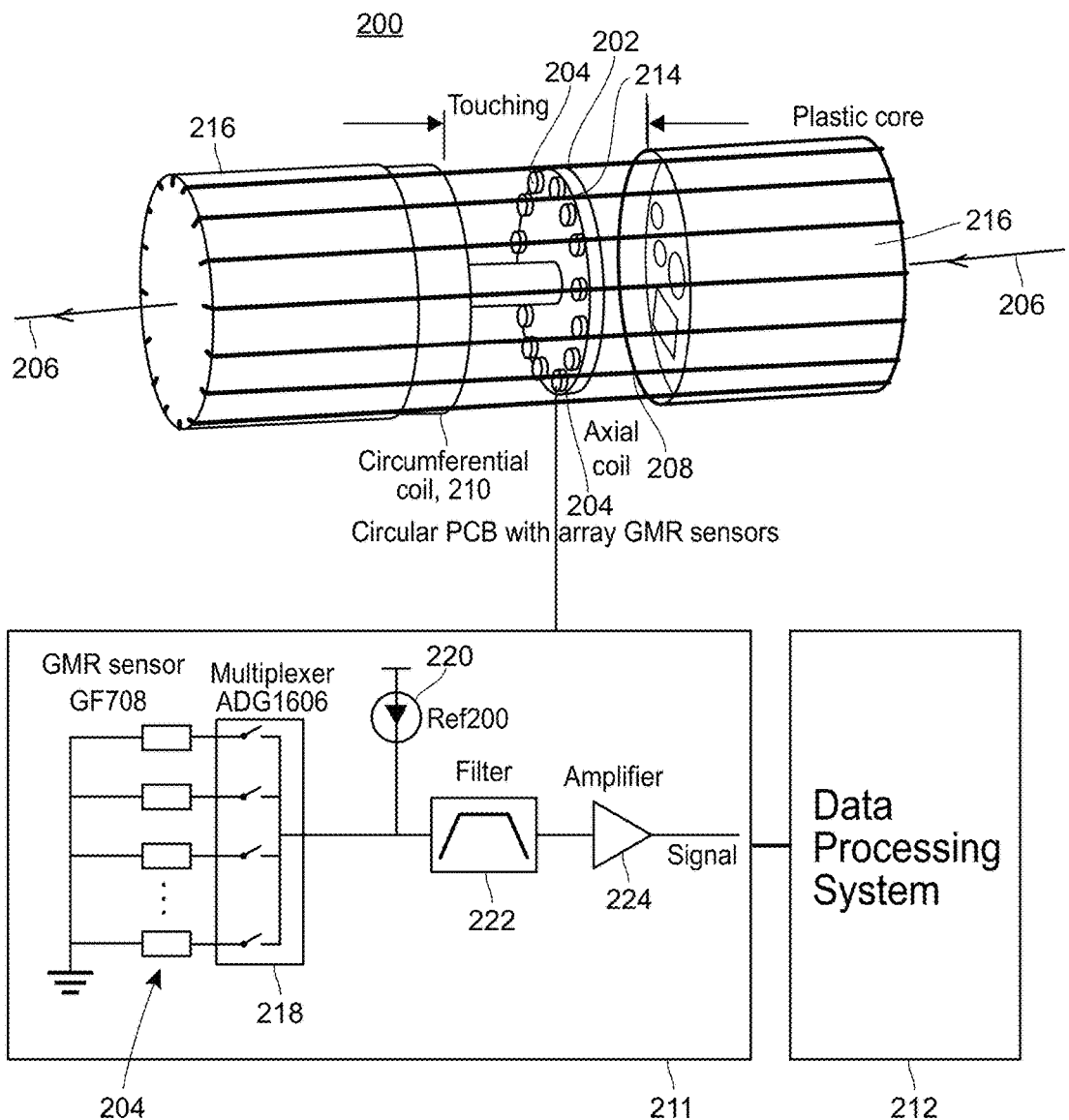
FIG. 11 illustrates an inspection probe with circumferential and axial excitation coil assemblies and magnetic field sensors for tube inspection, in accordance with another example.

FIG. 11 illustrates a probe 200 according to another configuration. The probe 200 has a sensor stage 202 having 16 GMR sensors 204 in a circumferential position about a central axis 206 of the probe 200. The probe 200 further includes orthogonally-oriented axial excitation coil winding 208 and circumferential coil winding 210. A signal conditioning circuit 211 is connected to the probe 200 along with a data acquisition and processing system 212.

In the illustrated example, the sensors 204 are positioned on a printed circuit board 214, with the sensitive direction of the GMR sensors 204 is along a radial axis, in which case the radial component of the magnetic field is measured. The axial and circumferential coil windings 208 and 210 were fabricated on a plastic 3D print core structure 216. The axial coil is as shown in FIGS. 3A and 3B. The circumferential coil was formed as a 12 turns bobbin coil. The circular PCB 214 housed the GMR sensors 204 and the circuit 211 and may be located inside the core. A two-phase current source was used to drive the circumferential and axial coils. The two phase currents are identical in frequency and 90° apart in phase.

The circuit 211 includes a multiplexer 218 connected to the GMR sensors 204. A DC constant current source 220 is provided and is used to drive the sensors 204. The variation of resistance of the GMR sensors is measured as a voltage signal according to equation (5), where $I_0$ is constant ($I_0$=100 μA), ΔR is change in GMR resistance, ΔV is the change in GMR sensor terminal voltage signal correlated with the field change.

$$\Delta V = I_0 \Delta R \tag{5}$$

The voltage signal is connected to a bandpass filter 222, with a bandpass range from 25 kHz to 500 kHz. The amplifier gain was 50, in this example. A lock-in amplifier 224 was used to recover the baseband signal and improve the signal-to-noise ratio. The in-phase and quadrature components of the signal were transferred from the lock-in amplifier to the data processing system 212, which includes one or more processors and one or more memories. The data processing system 212 may store and execute subroutines that control operation of the current source 220 that drives the sensors 204. The system 212 may store and execute subroutines that provide current the coil windings 208 and 210 to generate magnetic fields interacting with the tube wall. The data processing system 212 may further control a positioning system (not shown) that moves the probe 200 axially within the tube wall to scan for defects.

Figure 12:
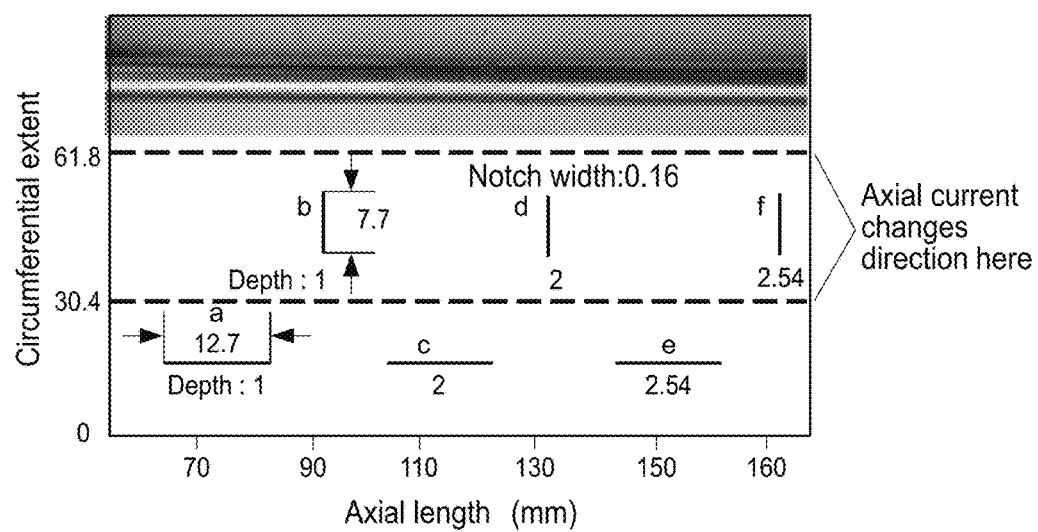
FIG. 12 illustrates a steam generator tube with different notches for testing of the probe of FIG. 11.

An Inconel 690 steam generator tube with machined axial and circumferential notches was inspected using the probe 200. The inner and outer radiuses of the tube were 9.84 mm, and 11.11 mm respectively. The machined notch dimensions and locations are shown in FIG. 12. The probe axial current changes direction along the dashed lines as shown in FIG. 12. The probe 200 was placed inside the tube in such a way that two of the sensors aligned with the dashed lines. The lift off distance from the excitation coils and GMR sensors to the inner surface of tube wall is about 0.44 mm and 1.44 mm respectively.

C-scan images of the axial notches are shown in FIGS. 13A-13F and the images of the circumferential notches are shown in FIGS. 14A-14F, showing that both axial and circumferential notches are detected by the probe 200. The magnitude of the signals from axial and circumferential notches are comparable, indicating that the probe 200 has similar levels of sensitivity to defects with different orientations.

Figure 15:
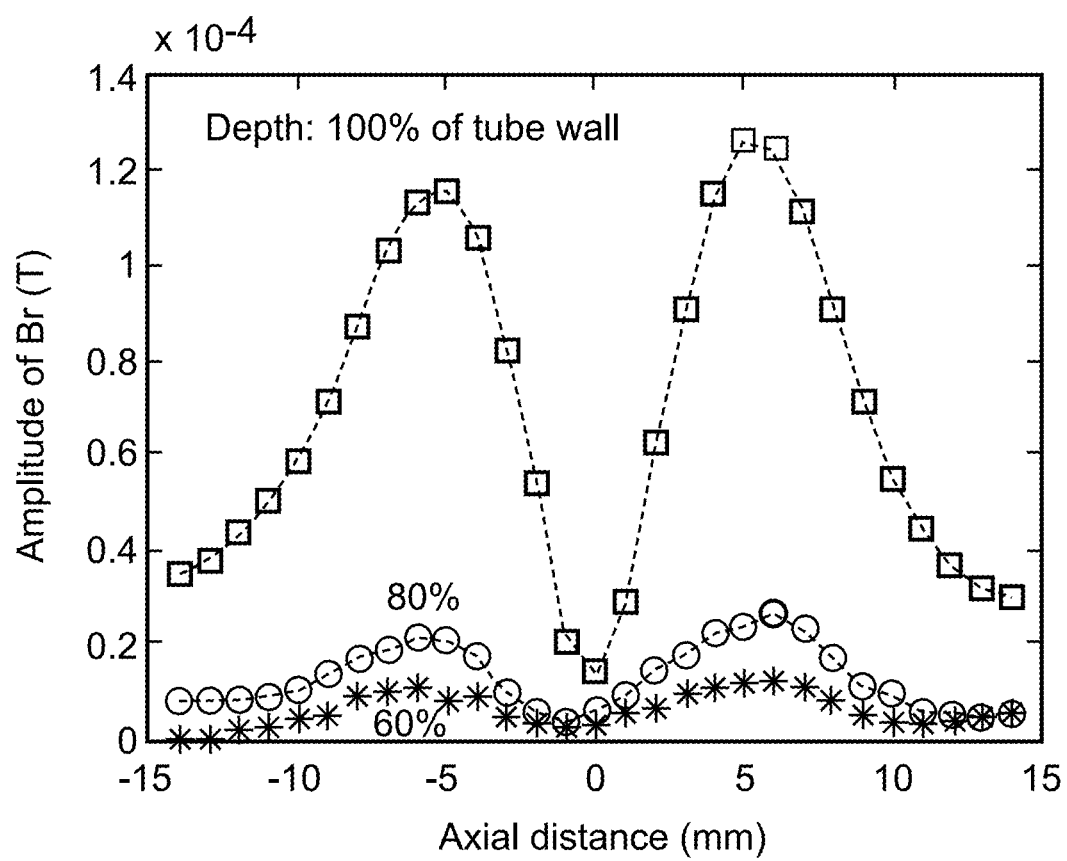
FIG. 15 illustrates the amplitude of an induced magnetic field along the axial direction through a defect center using the probe of FIG. 11.

To further analyze the data from notches of different depth, amplitude of $\overline{B}_r$ measured along a line scan through the C-scan data shown in FIG. 14 is presented in FIG. 15. It can be seen that the magnitude of the signal is positively correlated with the defect depth. These results can be compared with the simulation results shown in FIG. 10.

As shown, probe designs for tube inspection are provided that employ a rotating eddy current excitation scheme and an array of magnetic (e.g., GMR) sensors to measure the radial component of magnetic fields in a configuration in which the circumferential and axial coil windings are used Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner.

In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or that are permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or by processor-implemented hardware modules. The performance of certain of the operations may be distributed among the one or more processors, not only residing within a single machine (having different processing abilities), but also deployed across a number of machines. In some example embodiments, the processors may be located in a single location (e.g., deployed in the field, in an office environment, or as part of a server farm), while in other embodiments the processors may be distributed across a number of locations.

Unless specifically stated otherwise, discussions herein using words such as "processing," "computing," "calculating," "determining," "presenting," "displaying," or the like may refer to actions or processes on a GPU thread that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed:

1. An eddy current detection probe comprising:
   a circumferential coil assembly formed of a plurality of circumferentially extended coil windings, each circumferentially extended coil winding being spaced from adjacent circumferentially extended coil windings by a spacing distance, the circumferential coil assembly being positioned on an outer portion of the probe to induce circumferentially-extending eddy currents in a conductive vessel upon generating a circumferentially-probing magnetic field;
   an axial coil assembly formed of a plurality of axially extended coil windings, each axially extended coil winding being radially spaced apart from adjacent axially extended coil windings, the axial coil assembly being positioned on an outer portion of the probe to induce axially-extending eddy currents in the conductive vessel upon generating an axially-probing magnetic field, the circumferential coil assembly and the axial coil assembly being configured to receive respective current drive signals for generating the magnetic field; and
   a magnetic sensor array for detecting circumferentially-extending eddy currents and axially-extending eddy currents.

2. The eddy current detection probe of claim 1, wherein the axially extended coil windings share an axial center point of the probe.

3. The eddy current detection probe of claim 1, wherein the axial coil assembly is positioned on the interior of the circumferential coil assembly.

4. The eddy current detection probe of claim 1, wherein the axial coil assembly is positioned on the exterior of the circumferential coil assembly.

5. The eddy current detection probe of claim 1, wherein the axial coil assembly and the circumferential coil assembly are mounted to probe core support.

6. The eddy current detection probe of claim 1, wherein the magnet sensory array comprises a plurality of giant magnetoresistance (GMR) sensors.

7. The eddy current detection probe of claim 6, wherein the plurality of GMR sensors are positioned in the probe axially.

8. The eddy current detection probe of claim 6, wherein GMR sensors are mounted axially in a printed circuit board of the probe.

9. The eddy current detection probe of claim 1, further comprising a conditioning circuit comprising: a multiplexer connecting the sensors; a bandpass filter; and a lock-in amplifier.

10. The eddy current detection probe of claim 1, further comprising a circuit board comprising the multiplexer, the bandpass filter, the lock-in amplifier, and the magnetic sensory array.

11. The eddy current detection probe of claim 1, further comprising a position control element configured to move the probe along an axial direction of the conductive vessel, such that the probe senses for defects at different axial positions within the conductive vessel.

12. The eddy current detection probe of claim 1, further comprising a current source coupled to the circumferential coil assembly and the axial coil assembly.

* * * * *